(12) United States Patent
Ashton et al.

(10) Patent No.: US 10,478,353 B2
(45) Date of Patent: *Nov. 19, 2019

(54) ABSORBENT ARTICLE HAVING A FOLDED WAIST

(71) Applicant: The Procter & Gamble Company, Cincinnati, OH (US)

(72) Inventors: Gregory Ashton, Venice, FL (US); Eiro Fukuda, Mason, OH (US); Eric Patton Weinberger, Fairfield, OH (US); Daniel Clark Buchner, Chicago, IL (US)

(73) Assignee: The Procter & Gamble Plaza, Cincinnati, OH (US)

( * ) Notice: Subject to any disclaimer, the term of this patent is extended or adjusted under 35 U.S.C. 154(b) by 469 days.

This patent is subject to a terminal disclaimer.

(21) Appl. No.: 15/453,925

(22) Filed: Mar. 9, 2017

(65) Prior Publication Data

US 2017/0172817 A1    Jun. 22, 2017

Related U.S. Application Data

(63) Continuation of application No. 14/479,582, filed on Sep. 8, 2014, now Pat. No. 9,622,920, which is a
(Continued)

(51) Int. Cl.
*A61F 13/15* (2006.01)
*A61F 13/49* (2006.01)
(Continued)

(52) U.S. Cl.
CPC ...... *A61F 13/49011* (2013.01); *A61F 13/496* (2013.01); *A61F 13/49012* (2013.01);
(Continued)

(58) Field of Classification Search
CPC .......... A61F 13/15; A61F 13/47; A61F 13/53; A61F 13/51; C08L 77/00; A01K 23/00; A47L 13/17
See application file for complete search history.

(56) References Cited

U.S. PATENT DOCUMENTS 1,822,524 A   9/1931  Hendrix
2,703,577 A   3/1955  May
(Continued)

FOREIGN PATENT DOCUMENTS

EP    1 550 426 A      7/2005
WO    WO 96/18367 A    6/1996
WO    WO 2004/060230 A 7/2004

OTHER PUBLICATIONS

PCT International Search Report PCT/US2005/031158, dated Sep. 2, 2006, 11 pages.

*Primary Examiner* — Tatyana Zalukaeva
*Assistant Examiner* — Ilya Y Treyger
(74) *Attorney, Agent, or Firm* — Andrew J. Hagerty; Sarah M. DeCristofaro

(57) ABSTRACT

An article including a front region, a back region, and a chassis. The chassis may include an absorbent core having a front end edge and a back end edge. The front region and the back region may extend laterally outward beyond side edges of the chassis. The front region and the back region may abut to form a first seam and a second seam. At least one of the front region and the back region may include an elastic member. A first outer nonwoven layer of the front region and a second outer nonwoven layer of the back region may be folded to form an upper edge in the front and back regions such that a distal end of each of the first and second outer nonwoven layer may be disposed between the upper edge and the front and back end edges of the absorbent core, respectively.

5 Claims, 9 Drawing Sheets

Related U.S. Application Data continuation of application No. 14/257,323, filed on Apr. 21, 2014, now Pat. No. 9,522,088, which is a continuation of application No. 14/179,698, filed on Feb. 13, 2014, now abandoned, which is a continuation of application No. 11/650,155, filed on Jan. 5, 2007, now Pat. No. 8,672,914, which is a continuation of application No. 10/932,892, filed on Sep. 2, 2004, now abandoned.

(51) Int. Cl.
    *A61F 13/56*     (2006.01)
    *A61F 13/496*     (2006.01)
    *A61F 13/84*     (2006.01)
    *A61F 13/514*     (2006.01)
    *A61F 13/494*     (2006.01)
    *A61F 13/551*     (2006.01)
    *A61F 13/47*     (2006.01)
    *A61F 13/53*     (2006.01)
    *A61F 13/51*     (2006.01)
    *A61F 13/42*     (2006.01)

(52) U.S. Cl.
    CPC .. *A61F 13/49015* (2013.01); *A61F 13/49017* (2013.01); *A61F 13/4963* (2013.01); *A61F 13/49473* (2013.01); *A61F 13/51496* (2013.01); *A61F 13/5511* (2013.01); *A61F 13/55115* (2013.01); *A61F 13/565* (2013.01); *A61F 13/84* (2013.01); *A61F 2013/425* (2013.01); *A61F 2013/49493* (2013.01); *A61F 2013/8497* (2013.01)

(56) References Cited

U.S. PATENT DOCUMENTS

| | | |
|---|---|---|
| 2,866,459 A | 12/1958 | Sobelson |
| 3,441,025 A | 4/1969 | Ralph |
| 3,860,003 A | 1/1975 | Buell |
| 3,911,173 A | 10/1975 | Sprague |
| 3,929,135 A | 12/1975 | Thompson |
| 4,325,246 A | 4/1982 | Cooke |
| 4,342,314 A | 8/1982 | Radel et al. |
| 4,463,045 A | 7/1984 | Ahr et al. |
| 4,475,912 A | 10/1984 | Coates |
| 4,515,595 A | 5/1985 | Kievit et al. |
| 4,573,986 A | 3/1986 | Minetola et al. |
| 4,610,678 A | 9/1986 | Weisman et al. |
| 4,670,012 A | 6/1987 | Johnson |
| 4,673,402 A | 6/1987 | Weisman et al. |
| 4,681,581 A | 7/1987 | Coates |
| 4,695,278 A | 9/1987 | Lawson |
| 4,704,115 A | 11/1987 | Buell |
| 4,785,996 A | 11/1988 | Ziecker |
| 4,795,454 A | 1/1989 | Dragoo |
| 4,834,735 A | 5/1989 | Alemany et al. |
| 4,842,666 A | 6/1989 | Werenicz |
| 4,888,231 A | 12/1989 | Angstadt |
| 4,909,803 A | 3/1990 | Aziz et al. |
| D308,989 S | 7/1990 | Cohen |
| 4,940,464 A | 7/1990 | Van Gompel et al. |
| 4,981,480 A | 1/1991 | Gaudet et al. |
| 4,988,344 A | 1/1991 | Reising et al. |
| 4,988,345 A | 1/1991 | Reising |
| 4,995,873 A | 2/1991 | Knight |
| 5,006,394 A | 4/1991 | Baird |
| 5,036,978 A | 8/1991 | Frank et al. |
| 5,050,742 A | 9/1991 | Muckenfuhs |
| 5,054,619 A | 10/1991 | Muckenfuhs |
| 5,100,399 A | 3/1992 | Janson et al. |
| 5,106,385 A | 4/1992 | Allen et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,196,000 A | 3/1993 | Clear et al. |
| 5,234,423 A | 8/1993 | Alemany et al. |
| 5,242,436 A | 9/1993 | Weil et al. |
| 5,246,433 A | 9/1993 | Hasse |
| 5,285,540 A | 2/1994 | Putz |
| 5,304,162 A | 4/1994 | Kuen |
| 5,366,453 A | 11/1994 | Zehner et al. |
| 5,443,161 A | 8/1995 | Jonese |
| 5,503,076 A | 4/1996 | Yeo |
| 5,549,593 A | 8/1996 | Ygge et al. |
| 5,569,234 A | 10/1996 | Buell et al. |
| 5,690,627 A | 11/1997 | Clear et al. |
| 5,725,382 A | 3/1998 | Walter et al. |
| 5,772,649 A | 6/1998 | Siudzinski |
| 5,934,470 A | 8/1999 | Bauer et al. |
| 5,941,865 A | 8/1999 | Otsubo et al. |
| 5,989,236 A | 11/1999 | Roe et al. |
| 5,997,521 A | 12/1999 | Robles et al. |
| 6,352,528 B1 | 3/2002 | Weber et al. |
| 6,388,166 B1 | 5/2002 | Herrlein et al. |
| 6,443,940 B1 | 9/2002 | Ashton et al. |
| 6,569,136 B1 | 5/2003 | Tao et al. |
| 6,649,808 B1 | 11/2003 | Tao et al. |
| 6,733,483 B2 | 5/2004 | Raufman et al. |
| 6,830,566 B2 | 12/2004 | Kuen et al. |
| 8,206,366 B2 | 6/2012 | Datta et al. |
| 2001/0018579 A1 | 8/2001 | Klemp |
| 2003/0115837 A1 | 6/2003 | Zimmer et al. |
| 2003/0120240 A1 | 6/2003 | Buell et al. |
| 2003/0158532 A1 | 8/2003 | Magee et al. |
| 2004/0127876 A1 | 7/2004 | Stevens |
| 2004/0167489 A1 | 8/2004 | Kellenberger |
| 2004/0236299 A1 | 11/2004 | Tsang et al. |
| 2005/0027274 A1 | 2/2005 | Suzuki et al. |
| 2005/0175269 A1 | 8/2005 | Ashton et al. |
| 2005/0222549 A1 | 10/2005 | Balogh |

ABSORBENT ARTICLE HAVING A FOLDED WAIST

CROSS REFERENCE TO RELATED APPLICATIONS

This application is a continuation of U.S. application Ser. No. 14/479,582 filed on Sep. 8, 2014, which is a continuation of U.S. application Ser. No. 14/257,323 filed on Apr. 21, 2014, which is a continuation of U.S. application Ser. No. 14/179,698 filed on Feb. 13, 2014, which is a continuation of U.S. application Ser. No. 11/650,155, filed on Jan. 5, 2007, which is a continuation of U.S. application Ser. No. 10/932,892 filed on Sep. 2, 2004, the substances of which are incorporated herein by reference.

FIELD

The present invention relates to disposable absorbent articles such as pull-on garments. More specifically, the present invention relates to disposable pull-on garments having a foreshortened waist.

BACKGROUND

It has long been known that absorbent articles such as disposable diapers with fasteners, pull-on diapers, training pants, sanitary napkins, pantiliners, incontinence briefs, and the like, offer the benefit of receiving and containing urine and other bodily exudates. To effectively contain exudates, the articles should provide a snug fit around the waist and legs of a wearer. Articles such as conventional diapers generally include a front and rear waist section releasably connected by a fastening means. Application of a conventional diaper is usually performed by a caregiver with the wearer in a supine position. Such diapers allow for easy application by the caregiver but inhibit self-application by the wearer.

Disposable pull-on garments were developed, in part, to address the problem of self-application. Pull-ons effectively contain exudates while allowing for self-application. Such garments generally include a chassis comprising a liquid pervious bodyside liner, a liquid impervious outer cover, an absorbent core therebetween, and a pair of ears or side panels that are prejoined connecting the front and rear portions of the chassis. Pull-on garments have become popular for use on children who are able to walk and may be engaged in toilet training. Pull-on garments may serve as an intermediary product for the child between the wear of a conventional diaper and underwear. The pull-on provides a milestone for the child who may be involved in toilet training and developing independence from the caregiver. However, to be an effective advance over a conventional diaper, the pull-on should not only allow for self-application but should also provide a mechanism for easier self-application and encouragement to the child to apply the pull-on without the aid of the caregiver.

Unfortunately, current pull-on garments may be difficult for self-application by an infant. During self-application, a friction force exists opposing the motion or attempted motion of the pull-on. The friction force is increased as the pull-on is moved against the legs and torso of the wearer because of increased contacting surface area between the pull-on and the infant's skin. Pull-ons often have elasticized ears or side panels which further impede self-application by the infant. The elasticized side panels are often stretched as the pull-on rises up the infant's legs and torso. The stretching of the side panels results in an increased normal force against the infant's skin. An increase in the normal force results in an increase in the friction force. Consequentially, the increased friction force must be overcome by the child during self-application. In order to apply the pull-on in an ideal snug configuration, the infant may have difficulty in counteracting the increasing friction force.

Furthermore, the child's acceptance of the pull-on garment is important to successful toilet training. If the child views that the pull-on as more like underwear and less like a diaper, the pull-on successfully serves as an intermediary between diapers and underwear. However, existing pull-on garments may be perceived as more diaper-like than underwear-like if the garment must be applied by a caregiver instead of by the child alone or if excessive caregiver assistance is needed for successful application of the garment. Child acceptance of the pull-on can be improved by providing a pull-on garment that is easily self-applicable and, thus, more underwear-like.

Current pull-on garments often fail to provide the child with incentives for self-application. From a child's perspective, toilet training may be a long and difficult process. Keeping the child motivated throughout toilet training is important since the child may otherwise regress. One way of keeping the child motivated and engaged is by providing graphics on the external surfaces of the pull-on garment. Current graphics, however, are generally static throughout application. Essentially, the pull-on looks the same before application and immediately after application. A static graphic does little to motive or excite a child, and, as a result, the child may become bored with toilet training. A pull-on garment that changes in visual appearance during application can excite and motivate a child. As a result, the child is more likely to be engaged in toilet training.

SUMMARY

The present disclosure is directed to a pull-on wearable article including a front region, a back region opposite the front region, a crotch region, and a chassis. The chassis may include an absorbent core extending from the front region to the back region. The absorbent core may include a front end edge and a back end edge. The front region may extend laterally outward beyond side edges of the chassis and the back region may extend laterally outward beyond side edges of the chassis. Further, the front region may extend laterally outward beyond side edges of the chassis and the back region may extend laterally outward beyond side edges of the chassis. The front region may include a first front edge and a second front edge. The first front edge may extend in a direction parallel to the first central longitudinal axis, and the second front edge may extend in a direction parallel to the first central longitudinal axis. The back region may include a first back edge and a second back edge. The first back edge may extend in a direction parallel to the second central longitudinal axis, and the second back edge may extend in a direction parallel to the second central longitudinal axis. A portion of the front region and a portion of the back region may abut to form a first seam and a second seam such that the front region and the back region may be configured to form a continuous belt, a first leg opening, and a second leg opening. At least one of the front region and the back region may include an elastic member. The elastic member may include one or more strands. The article may also include a folded continuous belt portion comprising a fold and including at least a first outer nonwoven layer of the front region and at least a second outer nonwoven layer of the back region. The folded continuous belt portion may extend about a circumference of the continuous belt when positioned on the wearer. The folded continuous belt portion may comprise an upper edge coinciding with the fold in the front and back regions such that a distal end of each of the first and second outer nonwoven layers is disposed between the upper edge and the front and back end edges of the absorbent core, respectively. The folded continuous belt portion may comprise a first portion disposed in the front region and extending in a lateral direction between the first seam and the second seam and extending in a longitudinal direction between the upper edge and the distal end of the nonwoven outer layer. The first portion may have a first longitudinal distance measured from the upper edge to the distal end of the nonwoven outer layer. The folded continuous belt portion may comprise a second portion disposed in the back region and extending in a lateral direction between the first seam and the second seam and extending in the longitudinal direction between the upper edge and the distal end of the nonwoven outer layer. The second portion may have a second longitudinal distance measured from the upper edge to the distal end of the nonwoven outer layer. The first longitudinal distance may be substantially the same as the second longitudinal distance. The first seam may include a pattern of discrete spaced bonds extending in the longitudinal direction from the first leg opening to the upper edge. The second seam may include a pattern of discrete spaced bonds extending in the longitudinal direction from the second leg opening to the upper edge.

The present disclosure may also be directed to a pull-on wearable article including a front region, a back region opposite the front region, a longitudinal axis extending in a vertical direction and equally bisecting at least one of the front region and the back region, a crotch region disposed between the front region and the back region, and a chassis including an absorbent core extending from the front region to the back region. The absorbent core may include a front end edge and a back end edge. The front region may extend laterally outward beyond side edges of the chassis and the back region may extend laterally outward beyond side edges of the chassis. The front region may include a first front edge and a second front edge and the back region may include a first back edge and a second back edge. Each of the first front edge, the second front edge, the first back edge, and the second back edge may extend in a longitudinal direction parallel to the longitudinal axis. A portion of the front region and a portion of the back region may abut to form a first seam and a second seam such that the front region and the back region may be configured to form a continuous belt, a first leg opening, and a second leg opening. Further, at least one of the front region and the back region may include an elastic member. The article may also include a folded continuous belt portion comprising a fold and including at least a first outer nonwoven layer of the front region and at least a second outer nonwoven layer of the back region. The folded continuous belt portion may extend about a circumference of the continuous belt when positioned on the wearer. The folded continuous belt may include an upper edge in the front and back regions such that a distal end of each of the first and second outer nonwoven layer is disposed between the upper edge and the front and back end edges of the absorbent core, respectively. The upper edge may coincide with the fold. A longitudinal distance between the upper edge and the distal end of each of the first and second outer nonwoven layers may be substantially uniform about the folded continuous belt. The first seam may include a first pattern of discrete spaced bonds extending in the longitudinal direction from the first leg opening to the upper edge. The first pattern may include a first group of discrete spaced bonds and a second group of discrete spaced bonds. The second seam may include a second pattern of discrete spaced bonds extending in the longitudinal direction from the second leg opening to the upper edge. The second pattern may include a third group of discrete spaced bonds and a fourth group of discrete spaced bonds.

The present disclosure may also be directed to a pull-on wearable article including a front region, a back region opposite the front region, a crotch region disposed between the front region and the back region, and a chassis including an absorbent core extending from the front region to the back region. The absorbent core may include a front end edge and a back end edge. The front region may extend laterally outward beyond side edges of the chassis and the back region may extend laterally outward beyond side edges of the chassis. The front region may include a first front edge and a second front edge and the back region may include a first back edge and a second back edge. A portion of the front region and a portion of the back region may abut to form a first seam and a second seam such that the front region and the back region are configured to form a continuous belt, a first leg opening, and a second leg opening. At least one of the front region and the back region may include an elastic member. The article may also include a folded continuous belt portion including a fold and including at least a first outer nonwoven layer of the front region and at least a second outer nonwoven layer of the back region. The folded continuous belt portion may extend about a circumference of the continuous belt when positioned on the wearer. The folded continuous belt portion may include an upper edge in the front and back regions such that a distal end of each of the first outer nonwoven layer and the second outer nonwoven layer is disposed between the upper edge and the front and back end edges of the absorbent core, respectively. The folded continuous belt may include a first portion extending laterally between the first seam and the second seam and extending longitudinally between the upper edge and the distal end of the first outer nonwoven layer. The first portion has a first longitudinal distance measured from the upper edge to the distal end of the first outer nonwoven layer. The folded continuous belt may include a second portion extending laterally between the first seam and the second seam and extending longitudinally between the upper edge and the distal end of the second outer nonwoven layer. The second portion has a second longitudinal distance. Each of the first front edge, the second front edge, the first back edge, and the second back edge may extend in a longitudinal direction perpendicular to at least one of the distal end of the first outer nonwoven layer and the distal end of the second outer nonwoven layer. The first longitudinal distance may be substantially uniform relative to the second longitudinal distance. The first seam may include discrete spaced bonds extending in the longitudinal direction from the first leg opening to the upper edge. The second seam may include discrete spaced bonds extending in the longitudinal direction from the second leg opening to the upper edge.

DETAILED DESCRIPTION

Figure 1:
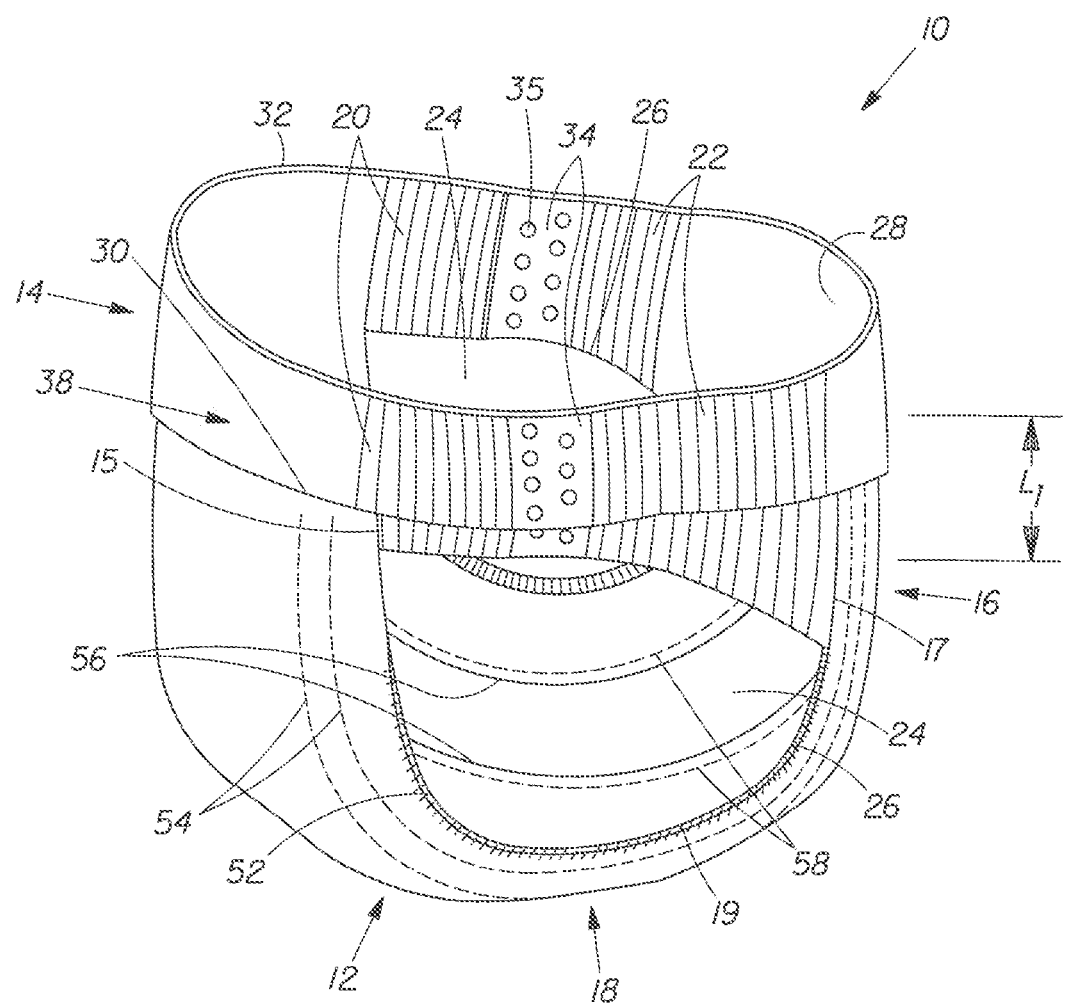
FIG. 1 is a perspective view of one embodiment of a disposable pull-on garment of the present invention in a pre-application state.

As used herein, the term "absorbent article" or "article" refers to wearable devices, which absorb and/or contain liquid, and more specifically, refers to devices, which are placed against or in proximity to the body of the wearer to absorb and contain the various exudates discharged from the body. Suitable examples include diapers, prefastened diapers, recloseable diapers, training pants, pull-on garments, adult incontinence products and feminine care products such as sanitary napkins.

As used herein, "pull-on garment" refers to articles of wear which have a defined waist opening and a pair of leg openings and which are pulled onto the body of the wearer by inserting the legs into the leg openings and pulling the article up over the waist.

As used herein, "disposable" describes garments which are not intended to be laundered or otherwise restored or reused as a garment (i.e., they are intended to be discarded after a single use and, preferably, to be recycled, composted or otherwise disposed of in an environmentally compatible manner).
and contain the various exudates discharged from the body.

As used herein, "pull-on diaper" refers to pull-on garments generally worn by infants and other incontinent individuals to absorb and contain urine and feces. It should be understood, however, that the present invention is also applicable to other absorbent articles.

As used herein, "panel" denotes an area or element of the pull-on garment. (While a panel is typically a distinct area or element, a panel may coincide (functionally correspond) or overlap an adjacent panel.)

As used herein, "joined" or "joining" encompasses configurations whereby an element is directly secured to another by affixing the element directly to the other element, and configurations whereby the element is indirectly secured to the other element by affixing the element to intermediate member(s) which in turn are affixed to the other element.

As used herein, the term "longitudinal" generally refers to a line, axis, or direction in the plane of the article that is generally aligned with (e.g., approximately parallel including directions within ±45° of the longitudinal direction) a vertical plane which equally bisects a standing wearer into left and right halves when the article is worn.

As used herein, the terms "lateral" or "transverse" refer to a line, axis or direction which lies within the plane of the pull-on garment that is generally perpendicular to the longitudinal direction.

As used herein, the term "foreshorten" means to reduce at least one linear dimension, most often length.

As used herein, the term "extensible" refers to materials that are capable of extending in at least one direction to a certain degree without undue rupture.

As used herein, the term "elasticity" and "elastically extensible" refer to extensible materials that have the ability to return to approximately their original dimensions after the force that extended the material is removed. Herein, any material or element described as "extensible" may also be elastically extensible unless otherwise provided.

As used herein, the term "post-application" refers to the state of an article as it would appear after being successfully and fully applied to a wearer such that the side panels are fully extended from the pre-application state.

As used herein, the term "side panel length" refers to the distance of the narrowest point of the pull-on garment between the top of the leg opening and the waist edge.

As used herein, the term "pre-application" refers to the state of the pull-on garment having a foreshortened side panel exhibiting a pre-application side panel length, $L_i$.

As used herein, a "pre-foreshortened side panel" refers to a side panel that does not require foreshortening by a wearer, a caregiver, or any other intermediary prior to application.

As used herein, the term "furl" means to fold, roll, coil, curl, pleat, ruffle, frill, crease, crimp, bend, gather, loop, shirr, or any other process by which the side panel length is reversibly foreshortened and combinations thereof.

As used herein, "wearer-facing surface" means a surface of the absorbent article or component of the absorbent article that is intended to be worn toward or adjacent to the body of the wearer.

As used herein, "garment facing surface" is on the opposite the wearer-facing surface and is intended to be worn toward or placed adjacent to the wearer's clothing or undergarments when the disposable absorbent article is worn.

Figure 2:
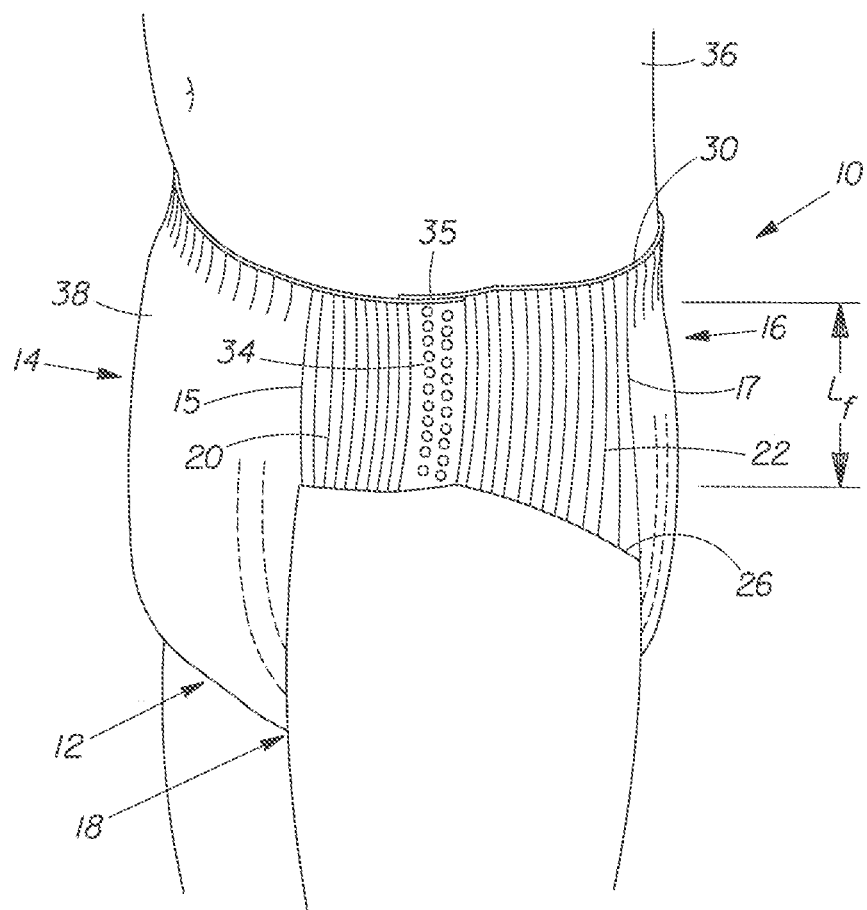
FIG. 2 is a perspective view of disposable pull-on garment of FIG. 1 in a post-application state.

FIGS. 1 and 2 show embodiments of an absorbent article as a pull-on garment according to the present invention. FIG. 1 shows one embodiment of a disposable pull-on garment 10 of the present invention in a pre-application configuration. The disposable pull-on garment 10 of the present invention comprises a chassis 12 that has a front region 14; a back region 16 and a crotch region 18 between the front region 14 and the back region 16. The front region 14 may have two opposing longitudinal edges 15. The back region 16 may have two opposing longitudinal edges 17. The crotch region 18 may have two opposing longitudinal edges 19. The garment 10 may include a gasketing leg cuff 52. The gasketing leg cuff may comprise one or more elastic strands 54. The garment may also include a barrier leg cuff 56. The barrier leg cuff 56 may comprise a spacing means 58 which may be one or more elastic strands.

The disposable pull-on garment 10 may include two front side panels 20 each extending laterally outward from the chassis along the front region longitudinal edge 15 and two back side panels 22 each extending laterally outward from the chassis along the back region longitudinal edge 17. The front and back side panels 20, 22 may be joined at a seam 34 to form two leg openings 24 and a waist opening 28. The front and back side panels may be joined by more than one discrete spaced bonding sites 35. The two leg openings 24 are defined by a leg opening edge 26. The waist opening 28 is defined by a waist edge 30. A continuous belt 38 is a circumferential region that may be defined by the side panels 20, 22 and the front and rear region of the chassis 12.

The side panels 20, 22 are shown as having been foreshortened. The side panels 20, 22 may be foreshortened during the manufacturing process of the garment. The side panels 20, 22 may be foreshortened by furling the continuous belt 38. The entire circumference of the continuous belt 38 or a portion thereof may be furled. The continuous belt 38 of the pull-on garment may be furled such that the waist edge 30 is not the uppermost circumferential edge of the garment 10. The uppermost circumferential edge of the pull-on garment may be an upper edge 32. It should be noted that in some embodiments of the present invention, the waist edge 30 may be the upper edge 32. It is desirable that the furled continuous belt 38 not obscure or obstruct the leg openings 24 such that application of the garment 10 is substantially hindered. The furled continuous belt 38 should not block more than about 75% of the leg opening 24. In one embodiment, the furled continuous belt 38 should block no more than about 50% of the leg opening 24. In one embodiment, the furled continuous belt 38 should block no more than 25% of the leg opening 24. In another embodiment, the furled continuous belt 38 will not obscure, obstruct, or block the leg opening 24.

In its pre-application state, the pull-on garment 10 exhibits a pre-application side panel length, $L_i$. The pre-application side panel length, $L_i$, is the longitudinal distance from the uppermost point along the leg opening 24 to the closest point on the upper edge 32, as measured along the garment-facing surface of the pull-on garment 10. The pre-application side panel length, $L_i$, is measured while the pull-on garment 10 is in a substantially relaxed state and prior to application. If, in the pre-application state, the furled continuous belt 38 obscures the leg opening 24, the pre-application side panel length, $L_i$, is still measured from the uppermost point along the leg opening 24 to the closest point on the upper edge 32. However, the uppermost point along the leg opening may be along or on the part of the furled continuous belt 38 that obscures the leg opening.

In one embodiment, the garment 10 is pre-foreshortened such that the side panels 20, 22 do not require foreshortening by a user (i.e., the garment 10 is already foreshortened).

FIG. 2 shows the pull-on garment 10 of FIG. 1 in its post-application state on the body of a wearer 36. In the post-application state, the pull-on garment 10 may be positioned for wear with the side panels 20, 22 fully extended and lengthened from the pre-application state. The continuous belt 38 may be unfurled so that the waist edge may become the upper edge of the pull-on garment. The pull-on garment 10 in the post-application state exhibits a post-application side panel length, $L_f$. The post-application side panel length, $L_f$, is the longitudinal distance from the uppermost point along the leg opening edge 26 to the closest point on the waist edge 30, as measured along the garment-facing surface of the pull-on garment 10. In one embodiment, the pull-on garment 10 may have a post-application side panel length $L_f$ that is greater than the post-application side panel length Li. In one embodiment, $L_f$ may be at least about 5% greater than $L_i$. In another embodiment, $L_f$ may be at least about 10% greater than $L_i$. In one embodiment, $L_f$ may be at least about 25% greater than $L_i$. In one embodiment, $L_f$ may be at least about 50% greater than $L_i$. In one embodiment, $L_f$ may be at least about 100% greater than $L_i$. In another embodiment, $L_f$ may be at least about 200% greater than $L_i$.

Figure 3A:
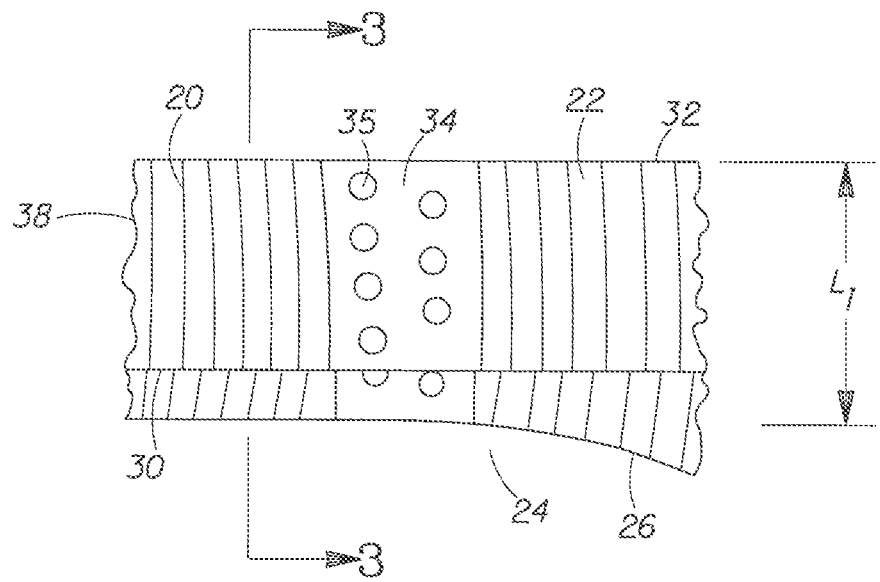
FIG. 3a is a detailed plan view of one embodiment of the foreshortened side wall.

FIG. 3a is an enlarged detailed plan view of the front and back side panels 20, 22 as shown in FIG. 1. The front side panel 20 and back side panel 22 are joined at the seam 34 to form the leg opening 24. The front and back side panels 20, 22 may be joined by more than one discrete spaced bonding sites 35. The leg opening 24 is defined by the leg opening edge 26. In this embodiment, the side panels are foreshortened by furling the continuous belt 38 of the pull-on garment with a single fold. The single fold results in the waist edge 30 being displaced as the uppermost circumferential edge of the garment 10. A pre-application side panel length $L_i$ may be measured along the surface of the pull-on garment 10 from uppermost point along the leg opening 24 to the closest point on the upper edge 32.

Figure 3B:
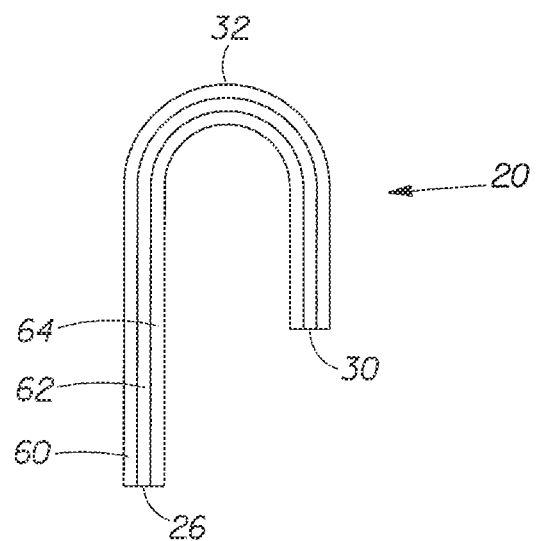
FIG. 3b is a cross-sectional view of the foreshortened side wall of FIG. 3a taken along sectional line 3-3.

FIG. 3b is a cross-sectional view taken along sectional line 3-3 of FIG. 3a. This cross-sectional view of the front side panel 20 illustrates furling by way of a single fold. The relative positions of the leg opening edge 26, waist edge 30, and the upper edge 32 for this particular embodiment are illustrated. FIG. 3b shows one embodiment for the construction of the side panel 20, 22 as a three layer laminate including an inner nonwoven layer 62, an outer nonwoven layer 64, and an elastic member 60 disposed between the inner nonwoven layer 62 and the outer nonwoven layer 64. As is described below, other embodiments for side panel 20, 22 construction are feasible and well-known. The three layer laminate as shown is exemplary.

While this embodiment describes furling the continuous belt with a single fold, it is clearly envisioned that the continuous belt 38 may be folded more than once. Multiple folds may be used to minimize the post-application side panel length, $L_f$, while avoiding obstruction of the leg opening 24. Furthermore, the length and orientation of one or more folds may be altered to achieve a desired pre-application side panel length, $L_i$.

Figure 4A:
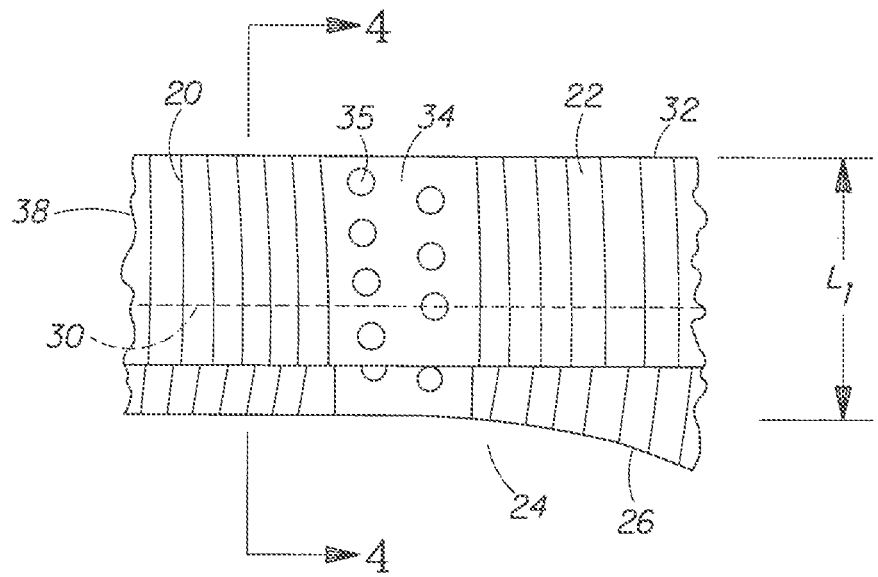
FIG. 4a is a detailed plan view of one embodiment of the foreshortened side wall.

FIG. 4a is an enlarged detailed plan view of the front and back side panels 20, 22 showing another embodiment of the foreshortened side panel. The front side panel 20 and back side panel 22 are joined at the seam 34 to form the leg opening 24. The front and back side panels 20, 22 may be joined by more than one discrete spaced bonding sites 35. The leg opening 24 is defined by the leg opening edge 26. In this embodiment, the side panels are foreshortened by furling the continuous belt 38 of the pull-on garment with multiple folds or rolls. The multiple folds or rolls results in the waist edge 30 being displaced as the uppermost circumferential edge of the garment 10. A pre-application side panel length $L_i$ may be measured along the surface of the pull-on garment 10 from uppermost point along the leg opening 24 to the closest point on the upper edge 32.

Figure 4B:
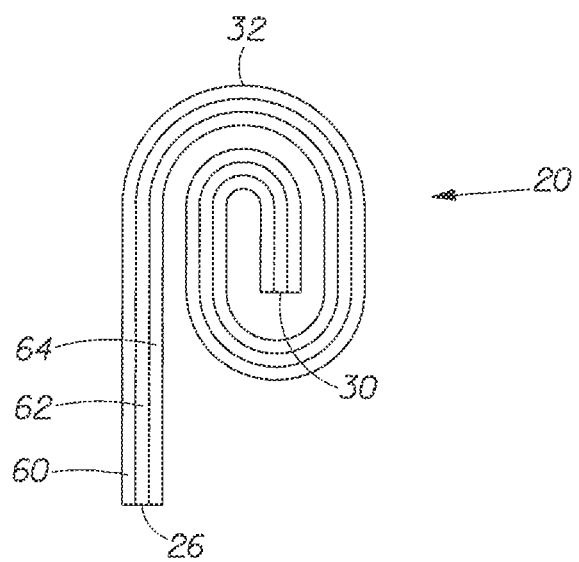
FIG. 4b is a cross-sectional view of the foreshortened side wall of FIG. 4a taken along sectional line 4-4.

FIG. 4b is a cross-sectional view taken along sectional line 4-4 of FIG. 4a. This cross-sectional view of the front side panel 20 illustrates furling by way of multiple folds or rolls. The relative positions of the leg opening edge 26, waist edge 30, and the upper edge 32 for this embodiment are illustrated. FIG. 4b shows one embodiment for the construction of the side panel as a three layer laminate including an inner nonwoven layer 62, an outer nonwoven layer 64, and an elastic member 60 disposed between the inner nonwoven layer 62 and the outer nonwoven layer 64. As is described below, other embodiments for side panel 20, 22 construction are feasible and well-known. The three layer laminate as shown is exemplary.

While this embodiment describes furling the continuous belt with three folds or approximately a 540° roll, it is clearly envisioned that the continuous belt 38 may be pre-application side panel length, $L_i$.

Figure 5A:
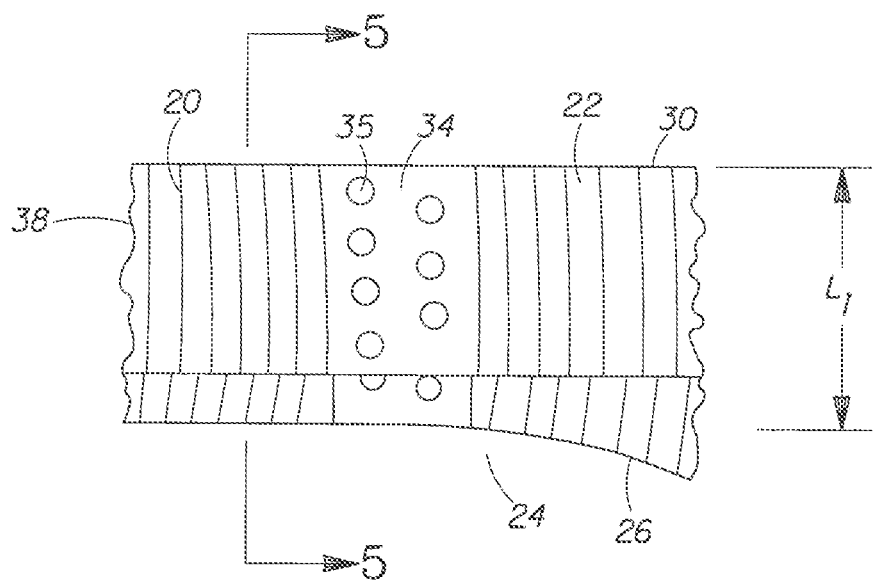
FIG. 5a is a detailed plan view of one embodiment of the foreshortened side wall.

FIG. 5a is an enlarged detailed plan view of the front and back side panels 20, 22 showing another embodiment of the foreshortened side panel. The front side panel 20 and back side panel 22 are joined at the seam 34 to form the leg opening 24. The front and back side panels 20, 22 may be joined by more than one discrete spaced bonding sites 35. The leg opening 24 is defined by the leg opening edge 26. In this embodiment, the side panels are foreshortened by furling the continuous belt 38 of the pull-on garment with longitudinal pleating. Specifically, the pleating is done with multiple reciprocating folds that are substantially parallel to the non-pleated surface of the pull-on (i.e., longitudinal pleats). In this embodiment, the longitudinal pleating may result in the waist edge 30 remaining as the uppermost circumferential edge of the garment 10. However, based on the length or orientation of the individual pleats, the waist edge 30 may be displaced (e.g., by an upper edge 32) as the uppermost edge of the garment 10. A pre-application side panel length Li may be measured along the surface of the pull-on garment 10 from uppermost point along the leg opening 24 to the closest point on the waist edge 30. In an alternate embodiment where the waist edge has been displaced as the uppermost edge of the garment 10, the pre-application side panel length Li may be measured from the uppermost point along the leg opening 24 to the closest point on the upper edge.

Figure 5B:
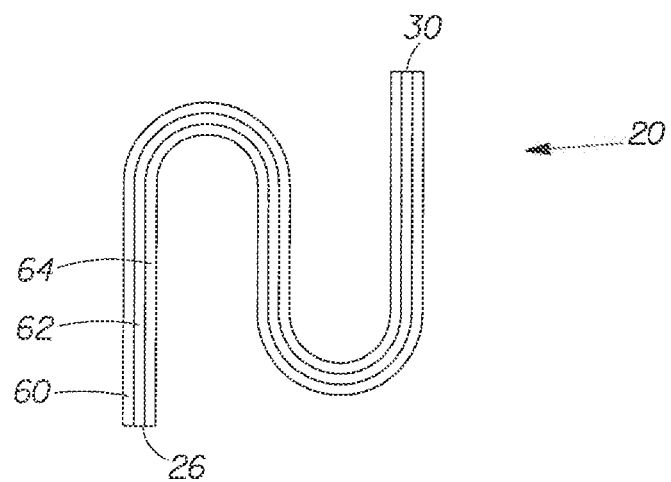
FIG. 5b is a cross-sectional view of the foreshortened side wall of FIG. 5a taken along sectional line 5-5.

FIG. 5b is a cross-sectional view taken along sectional line 5-5 of FIG. 5a. This cross-sectional view of the front side panel 20 illustrates furling by way of two longitudinal pleats. The relative positions of the leg opening edge 26 and waist edge 30 for this embodiment are illustrated. FIG. 5b shows one embodiment for the construction of the side panel as a three layer laminate including an inner nonwoven layer 62, an outer nonwoven layer 64, and an elastic member 60 disposed between the inner nonwoven layer 62 and the outer nonwoven layer 64. As is described below, other embodiments for side panel 20, 22 construction are feasible and well-known. The three layer laminate as shown is exemplary.

While this embodiment describes furling the continuous belt with two pleats, it is clearly envisioned that the continuous belt 38 may be pleated with pleats of varying number, configuration, and/or length to achieve a desired pre-application side panel length, Li.

Figure 6A:
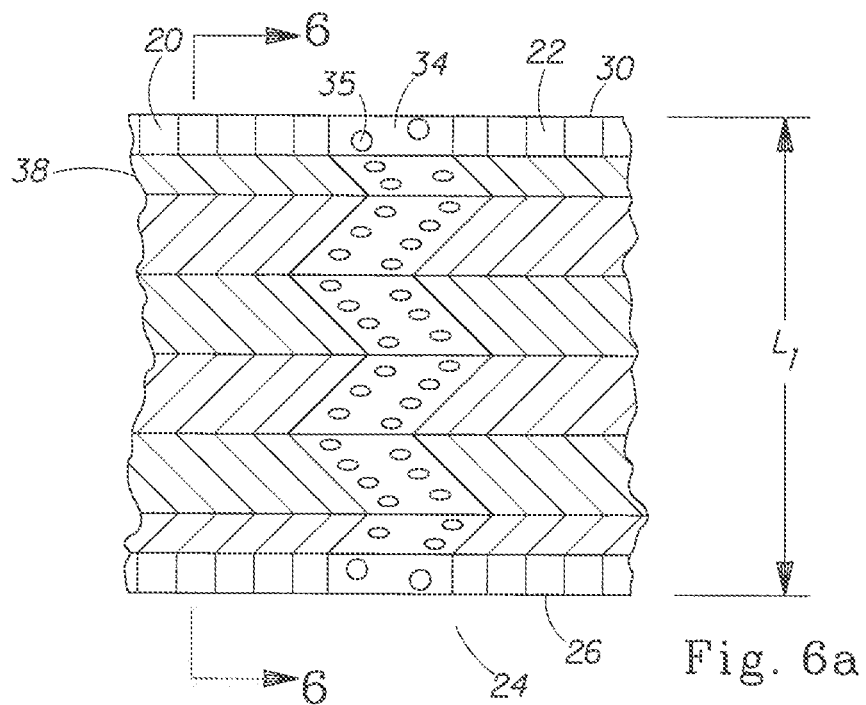
FIG. 6a is a detailed plan view of one embodiment of the foreshortened side wall.

FIG. 6a is an enlarged detailed plan view of the front and back side panels 20, 22 showing another embodiment of the foreshortened side panel. The front side panel 20 and back side panel 22 are joined at the seam 34 to form the leg opening 24. The front and back side panels 20, 22 may be joined by more than one discrete spaced bonding sites 35. The leg opening 24 is defined by the leg opening edge 26. In this embodiment, the side panels are foreshortened by furling the continuous belt 38 of the pull-on garment with transverse pleating. Specifically, the pleating is done with multiple reciprocating folds that are substantially perpendicular to the non-pleated surface of the pull-on (i.e., lateral pleats). In this embodiment, the lateral pleating may result in the waist edge 30 remaining as the uppermost circumferential edge of the garment 10. However, based on the length or orientation of the individual pleats, the waist edge 30 may be displaced as the uppermost edge of the garment 10. A pre-application side panel length Li may be measured along the surface of the pull-on garment 10 from uppermost point along the leg opening 24 to the closest point on the waist edge 30. In an alternate embodiment where the waist edge 30 has been displaced as the uppermost edge of the garment 10, the pre-application side panel length $L_i$ may be measured from the uppermost point along the leg opening to the closest point on the upper edge.

Figure 6B:
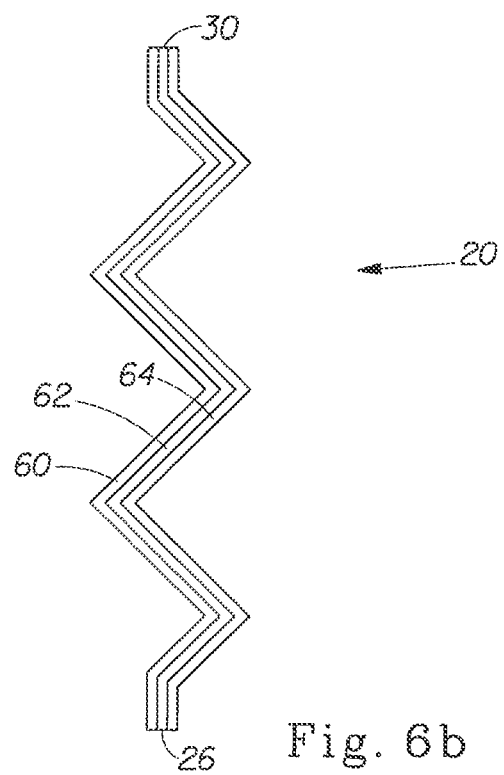
FIG. 6b is a cross-sectional view of the foreshortened side wall of FIG. 6a taken along sectional line 6-6.

FIG. 6b is a cross-sectional view taken along sectional line 6-6 of FIG. 6a. This cross-sectional view of the front side panel 20 illustrates furling by way of five lateral pleats. The relative positions of the leg opening edge 26 and waist edge 30 for this embodiment are illustrated. FIG. 6b shows one embodiment for the construction of the side panel 20 as a three layer laminate including an inner nonwoven layer 62, an outer nonwoven layer 64, and an elastic member 60 disposed between the inner nonwoven layer 62 and the outer nonwoven layer 64. As is described below, other embodiments for side panel 20, 22 construction are feasible and well-known. The three layer laminate as shown is exemplary.

While this embodiment describes furling the continuous belt with five pleats, it is clearly envisioned that the continuous belt 38 may be pleated with pleats of varying number, configuration, and/or length to achieve a desired pre-application side panel length, Li.

Figure 7:
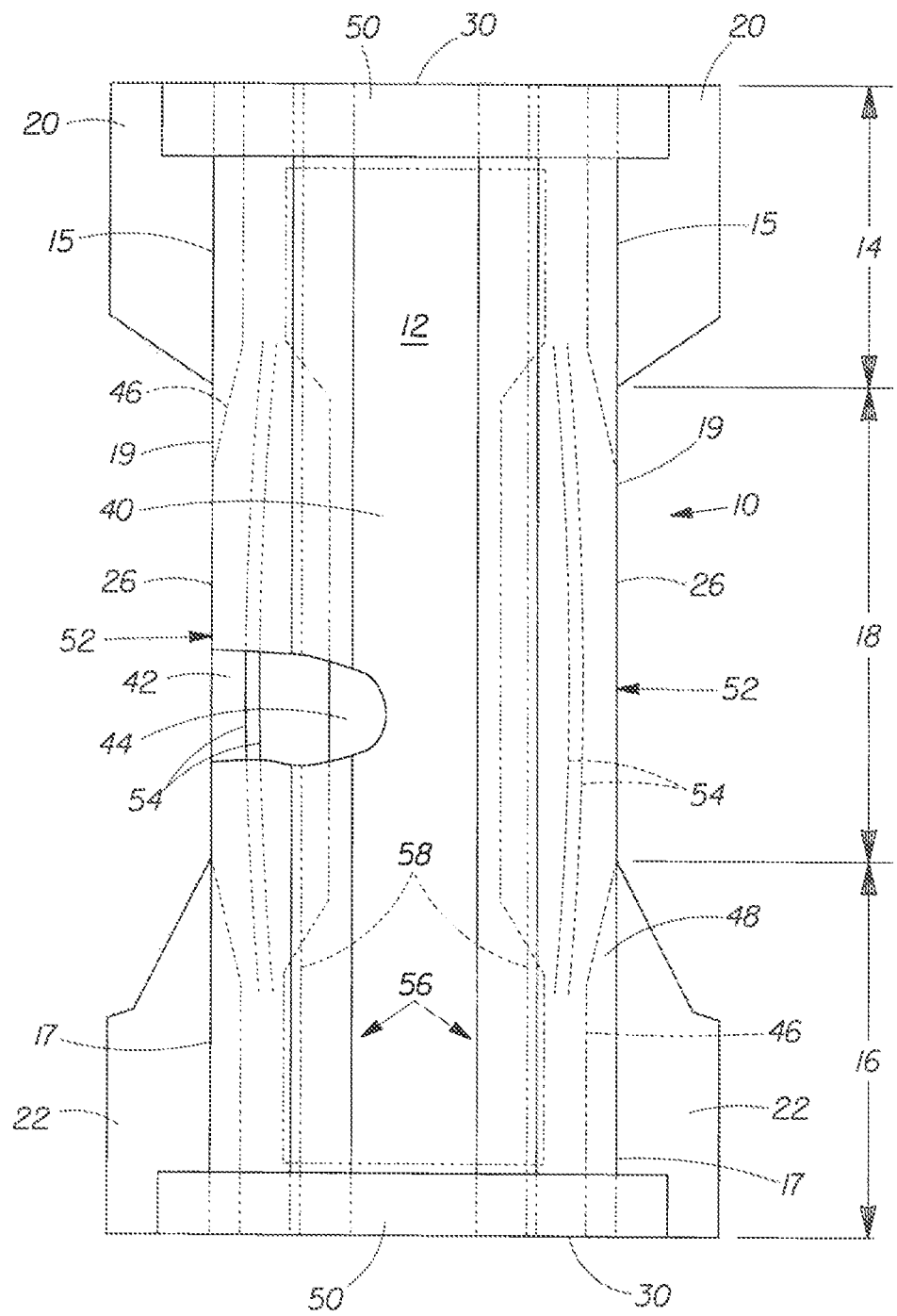
FIG. 7 is a plan view of a disposable pull-on garment.

FIG. 7 shows an exemplary pull-on garment in a partially cut-away plan view of the wearer-facing surface. The disposable pull-on garment 10 may comprise a chassis 12 that may have a front region 14; a back region 16 and a crotch region 18 between the front region 14 and the back region 16. The front region 14 may have two opposing longitudinal edges 15. The back region 16 may have two opposing longitudinal edges 17. The crotch region 18 may have two opposing longitudinal edges 19. The garment may have a waist edge 30 and a leg opening edge 26. A continuous belt 38 may be formed by side panels 20, 22 and the front and back region of the chassis 12 when the front side panels 20 are joined to the back side panels 22.

The chassis 12 may include a liquid pervious topsheet 40, a backsheet 42 joined with the topsheet 40, and an absorbent core 44 disposed between the topsheet 40 and the backsheet 42. The pull-on garment 10 may include at least two side panels 20, 22. The side panels 20, 22 may extend laterally outward from the front region longitudinal edges 15 and the back region longitudinal edges 17, respectively. The side panels 20, 22 may be joined to one another.

In one embodiment, the back side panels 22 may extend from the back region longitudinal edge 17 and may be joined to the corresponding front region longitudinal edge 15. Alternatively, the front side panels 20 may extend from the front region longitudinal edge 15 and may be joined to the corresponding back region longitudinal edge 17.

The side panels 20, 22 may be bonded directly or indirectly to each other and/or to the other elements of the chassis (e.g., topsheet, backsheet, and the like) in a variety of configurations including but not limited to an overlapped structure or an abutting structure. The bonding can be performed by any suitable means known in the art appropriate for the specific materials employed. Thus, sonic sealing, heat sealing, pressure bonding, adhesive or cohesive bonding, sewing, autogeneous bonding, and the like may be appropriate techniques. The bonding may by a predetermined pattern of heat/pressure or ultrasonic welds which withstands the forces and stresses generated on the garment during wear. Bonding may be performed by a plurality of discrete spaced apart seaming bonds 35 (as shown in FIG. 1). In an alternative embodiment, the bonding may be performed by a continuous bond which continuously bonds the side panels 20, 22. In another embodiment, the bonding may be by way of refastenable bonds such as adhesive bonds, cohesive bonds, and/or fasteners (e.g., hook and loop fastener).

The side panels 20, 22 may be elastically extensible in at least the lateral direction. In alternative embodiments, the side panels 20, 22 are elastically extensible both in the lateral and longitudinal directions. Extensible side panels 20, 22 may provide a more comfortable and contouring fit by initially conformably fitting the pull-on garment to the wearer and sustaining this fit throughout the time of wear well past when the pull-on garment has been loaded with exudates since the side panels 20,22 allow the sides of the pull-on garment to expand and contract.

The side panels 20, 22 may be formed by unitary elements of the pull-on garment 10 (i.e., they are not separately manipulative elements secured to the pull-on garment 10, but rather may be formed from and may be extensions of one or more of the various layers of the pull-on garment). The side panels 20, 22 may include at least one unitary element or a continuous sheet material, such as a nonwoven outer cover, that forms a part of the chassis 12 and continuously extends into the side panels 20, 22. Alternatively, the side panels 20, 22 may be discrete members which do not have any unitary element that forms a part of the chassis 12, and may be formed by joining the discrete members to the longitudinal edge of the chassis 12 in the front or back region.

The garment 10 may include side panels 20, 22 constructed from an elastic member 60 (as illustrated in FIGS. 3b, 4b, 5b, and 6b). The elastic member 60 may be extensible in at least one direction, typically in the lateral direction to generate a retention (or sustained) force that is optimal to prevent the pull-on garment 10 from drooping, sagging, or sliding down from its position on the torso without causing the red marking on the skin of the wearer. The elastic member 60 may be formed from a wide variety of materials and in a wide variety of sizes, forms and shapes. For example, the elastic member 60 may be in the form of a continuous planar layer. The continuous planar layer may include scrims, perforated (or apertures formed) films, elastomeric wovens or nonwovens, and the like. The continuous planar layer may take any shape which can be suitably provided in the side panels. Generally, the elastic member 60 is the same shape and size as the side panel 20, 22. In another embodiment, the elastic member 60 may be in the form of discrete strands (or strings) which are not connected each other.

In one embodiment, the elastic member 60 may be formed from a porous, macroscopically-expanded, three-dimensional elastomeric web as described in U.S. Patent Application Publication No. US 2003/0120240 A1 to Buell et al. A suitable porous elastomeric material 124 is manufactured by the Tredegar Film Products under the designation X-25007.

In one embodiment, the elastic member 60 may be formed from a scrim as described in U.S. Patent Application Publication No. US 2003/0120240 A1 to Buell et al. A suitable elastomeric scrim 124 is manufactured by the Conwed Plastics Company (Minneapolis, Minn., U.S.A.) under the designation X02514.

The elastic member 60 may be formed from other suitable elastomeric materials include synthetic or natural rubber, other synthetic or natural rubber foams, elastomeric films (including heat shrinkable elastomeric films), elastomeric woven or nonwoven webs, elastomeric composites, or the like.

In another embodiment, the side panel may include an elastic member 60 joined to at least one nonwoven web. For example, the elastic member 60 may be disposed between an inner nonwoven layer 62 and the outer nonwoven layer 64 (as illustrated in FIGS. 3b, 4b, 5b, and 6b). The elastic member 60 and nonwoven layer 62, 64 should maintain elastic extensibility in at least one direction. In some embodiments, the outer nonwoven layer 64 is a nonwoven outer cover 48 which, as described below, forms part of the backsheet 42.

Several well-known methods exist for making stretchable elastomeric/nonwoven laminate for use as the side panels 20, 22. For example, stretch-bonding involves stretching of the elastic member in a desired direction, laminating the stretched elastic member to one or more nonwovens, and releasing the tensioning force form the elastic member so that the nonwovens gather and exhibit corrugations. For anther example, neck-bonding involves stretching the nonwoven substrate(s) in a first direction such that the nonwoven substrate(s) necks (i.e., reduces linear dimension) in a direction perpendicular to the first direction. The elastic member is bonded to the stretched, necked nonwoven(s). The resulting laminate will exhibit stretch up to the original width of the nonwoven prior to necking. Combinations of stretch-bonding and neck-bonding are known to deliver multi-directional stretch.

Another well-known method for making the stretchable elastomeric/nonwoven laminate for use as the side panels 20, 22 is a zero-strain process. The zero-strain process involved bonding the elastic member and nonwoven together in an unstrained state. The elastomeric/nonwoven laminate is incrementally stretched to impart stretch properties. The zero-strain process is further described in U.S. Pat. No. 5,167,897 issued to Weber et al.; U.S. Pat. No. 5,156,793, issued to Buell et al.; and U.S. Pat. No. 5,143,679 issued to Weber et al.

The absorbent core 44 may be any absorbent member which may be generally compressible, conformable, non-irritating to the wearer's skin, and capable of absorbing and retaining liquids such as urine and other certain body exudates. The absorbent core 44 may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 44 may vary (e.g., the absorbent core 44 may have varying caliper zones, a hydrophilic gradient, a superabsorbent gradient, or lower average density and lower average basis weight acquisition zones; or may include one or more layers or structures). Further, the size and absorbent capacity of the absorbent core 44 may also be varied to accommodate wearers ranging from infants through adults. However, the total absorbent capacity of the absorbent core 44 should be compatible with the design loading and the intended use of the garment 10.

One embodiment of the garment 10 may have an asymmetric, modified hourglass-shaped absorbent core 44 having ears in the front and back waist regions 14, 16. Other exemplary absorbent structures for use as the absorbent core 44 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Other exemplary core configurations include dual core systems are disclosed in U.S. Pat. No. 5,234,423 issued to Alemany et al. on Aug. 10, 1993; U.S. Pat. No. 5,147,345 issued to Young et al. on Sep. 15, 1992; and U.S. Pat. No. 6,388,166 issued to Herrlein on May 14, 2002.

The topsheet 40 is preferably compliant, soft feeling, and non-irritating to the wearer's skin. Further, the topsheet 40 is preferably liquid pervious permitting liquids (e.g., urine) to penetrate readily through its thickness. A suitable topsheet 40 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. The topsheet 40 may be made of a hydrophobic material to isolate the wearer's skin from liquids which have passed through the topsheet 40 and are contained in the absorbent core 44 (i.e., to prevent rewet). If the topsheet 40 is made of a hydrophobic material, at least a portion of the upper surface of the topsheet 40 may be treated to be hydrophilic so that liquids will transfer through the topsheet more rapidly. This diminishes the likelihood that body exudates will flow off the topsheet 40 rather than being drawn through the topsheet 40 and being absorbed by the absorbent core 44. The topsheet 40 can be rendered hydrophilic by treating it with a surfactant. Suitable methods for treating the topsheet 40 with a surfactant include spraying the topsheet 40 material with the surfactant and immersing the material into the surfactant. A more detailed discussion of such a treatment and hydrophilicity is contained in U.S. Pat. No. 4,988,344 issued to Reising, et al. on Jan. 29, 1991 and U.S. Pat. No. 4,988,345 issued to Reising on Jan. 29, 1991.

In one embodiment, the topsheet 40 may be a nonwoven web that can provide reduced tendency for surface wetness; and consequently facilitate maintaining urine absorbed by the core 44 away from the user's skin, after wetting. One suitable topsheet material is a thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another suitable topsheet material is a thermobonded carded web which is available as Code No. Profleece Style 040018007 from Amoco Fabrics, Inc. (Gronau, Germany).

Another preferred topsheet 40 includes an apertured formed film. Apertured formed films are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 "Multilayer Polymeric Film" issued to Baird on Apr. 9, 1991.

The backsheet 42 may preferably be liquid impervious. The backsheet 42 may include a liquid impervious film 46. Preferably, the liquid impervious film 46 longitudinally spans the front, back and crotch regions 14, 16, and 18. In one embodiment, the liquid impervious film 46 does not laterally extend to the side panels 20, 22. The liquid impervious film 46 is impervious to liquids (e.g., urine) and may be manufactured from a thin plastic film. Preferably, such plastic films will permits vapors to escape from the garment 10. In a preferred embodiment, a microporous polyethylene film may be used for the liquid impervious film 46. A suitable microporous polyethylene film is manufactured by Mitsui Toatsu Chemicals, Inc., Nagoya, Japan and marketed as PG-P.

A suitable material for the liquid impervious film 46 may be a thermoplastic film having a thickness of from about 0.012 mm (0.5 mil) to about 0.051 mm (2.0 mils), preferably including polyethylene or polypropylene. Preferably, the liquid impervious film has a basis weight of from about 5 $g/m^2$ to about 35 $g/m^2$. However, it should be noted that other flexible liquid impervious materials may be used. Flexible materials are materials which are compliant and will readily conform to the general shape and contours of the wearer's body.

In some embodiments, the backsheet 42 further includes the nonwoven outer cover 48 which is joined with a garment-facing surface of the liquid impervious film 46 to form a laminate (i.e., the backsheet 42). The nonwoven outer cover 48 is preferably positioned at the outermost portion of the garment 10. The nonwoven outer cover 48 may span at least a portion of the outermost portion of the garment 10. In a preferred embodiment, the nonwoven outer cover 48 may cover substantially all of the area of the outermost portion of the garment 10. The nonwoven outer cover 48 may be joined to the liquid impervious film 46 by any suitable attachment means known in the art. For example, the nonwoven outer cover 48 may be secured to the liquid impervious film 46 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H.B. Fuller Japan Co., Ltd., Osaka, Japan as JM-6064.

In one embodiment, the nonwoven outer cover 48 may be a carded nonwoven web, for example, obtainable from Havix Co., LTD., Gifu, Japan as E-2341. The nonwoven outer cover 48 is made of bi-component fibers of a polyethylene (PE) and a polypropylene (PP). The ratio of PE/PP is about 50/50. The PE/PP bi-component fiber has the dimension of 2 dtex×51 mm. Another preferred carded nonwoven web is obtainable from Chisso Corp., Moriyama, Japan. The nonwoven outer cover 48 is also made of bi-component fibers of a polyethylene (PE) and a polypropylene (PP). The ratio of PE/PP is about 50/50.

In another embodiment, the nonwoven web is a spunbonded nonwoven web, for example, obtainable from Mitsui Petrochemical Industries, Ltd., Tokyo, Japan. The nonwoven web is made of bi-component fibers of a polyethylene (PE)

and a polypropylene (PP). The ratio of PE/PP is about 80/20. The PE/PP bi-component fiber has a thickness of approximately 2.3 dtex.

The backsheet 42 may be positioned adjacent the garment-facing surface of the absorbent core 44 and is preferably joined thereto by any suitable attachment means known in the art. For example, the backsheet 42 may be secured to the absorbent core 44 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., U.S.A., and marketed as HL-1358J. An example of a suitable attachment means involves an open pattern network of filaments of adhesive is disclosed in U.S. Pat. No. 4,573,986 issued to Minetola et al. on Mar. 4, 1986. Another suitable attachment means involves several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art. However, in other embodiments, the absorbent core 44 is not joined to the backsheet 42 and/or the topsheet 40 in order to provide greater extensibility in the front region 14 and the back region 16.

The pull-on garment 10 may further include gasketing leg cuffs 52 for improved containment of liquids and other body exudates. The gasketing leg cuffs 52 may include several different embodiments for reducing the leakage of body exudates in the leg regions. (The leg cuffs can be and are sometimes also referred to as leg bands, side flaps, barrier cuffs, elastic cuffs, or elasticized cuffs.) As shown in FIG. 7, the gasketing cuffs may include one or more elastic strands 54 or like material so as to provide a snug fit and, ideally, a seal impervious to bodily exudates.

The garment 10 may further include inner barrier cuffs 54 for improved containment of liquids and other body exudates. The inner barrier cuffs may include a spacing means 58 such as an elastic element as described in the below-referenced U.S. Pat. No. 4,909,803.

Exemplary gasketing and/or barrier cuff construction is disclosed in U.S. Pat. No. 3,860,003 issued to Buell on Jan. 14, 1975; U.S. Pat. No. 4,909,803 issued to Aziz et al. on Mar. 20, 1990; U.S. Pat. No. 4,695,278 issued to Lawson on Sep. 22, 1987; U.S. Pat. No. 4,795,454 issued to Dragoo on Jan. 3, 1989; and U.S. Pat. No. 4,704,115 issued to Buell on Nov. 3, 1987.

The pull-on garment 10 may further include an elasticized waist feature 50 that provides improved fit and containment. The elasticized waist feature 50 is that portion or zone of the pull-on garment 10 which is intended to elastically expand and contract to dynamically fit the wearer's waist. The elasticized waist feature 50 preferably extends longitudinally outwardly from the waist edge of the pull-on garment 10 toward the waist edge of the absorbent core 44. Preferably, the pull-on garment 10 has two elasticized waist features 50, one positioned in the back region 16 and one positioned in the front region 14, although other pull-on diaper embodiments can be constructed with a single elasticized waist feature. The elasticized waist feature 50 may be constructed in a number of different configurations including those described in U.S. Pat. No. 4,515,595 issued to Kievit et al. and U.S. Pat. No. 5,151,092 issued to Buell.

In one embodiment, the pull-on garment 10 of the present invention further includes at least one graphic on a garment-facing surface of the absorbent article. A graphic is any design, pattern, text, picture, or the like that is visible or can be made visible on the garment. In one embodiment, the pull-on garment may include a backsheet that comprises the graphic. In one particular embodiment, the garment of the present invention comprises a backsheet made from a microporous polymer film with registered graphics as described in U.S. Pat. No. 6,649,808 issued to Tao et al. on Nov. 18, 2003. A preferred embodiment has the garment of the present invention comprising a backsheet as described in U.S. Pat. No. 6,569,136 issued to Tao et al. on Nov. 18, 2003. Methods of imparting a graphic upon an absorbent article are well known in the art. For example, U.S. Pat. No. 5,503,076 issued to R. S. Yeo on Apr. 2, 1996 describes a multi-color printed nonwoven laminate and a process for producing the laminate; such a nonwoven may be used as a nonwoven cover on the pull-on garment of the present invention. Furthermore, graphics may be printed on other elements of the garment (e.g., nonwoven cover, backsheet, side, etc.) by printing techniques that are well known in the art including flexographic, ink jet, and gravure printing.

To encourage proper application of the garment and particularly self-application, the garment may include a hidden graphic either alone or in addition to a visible graphic (i.e., graphic that is visible on the garment in the pre-application state). A hidden graphic is a graphic that is not visible upon inspection of the garment while the garment is in its pre-application state but becomes visible in the extended post-application state of the garment. The hidden graphic provides a visual cue to the wearer that the pull-on garment has been properly unfurled and is in a post-application state. Furthermore, the hidden graphic may provide positive reinforcement to a wearer who may be engaged in a toilet training process. The hidden graphic may provide incentive for the wearer to dress himself or herself, which is often a component of the toilet training process.

In another embodiment, it may be desirable to have at least one visible graphic and at least one hidden graphic on the pull-on garment in its pre-application state. The visible graphic and the hidden graphic may be interactively interrelated. As used herein, the term "interactively interrelated" means that the visible graphic and the hidden graphic on a pull-on garment in the pre-application state are associated such that the hidden graphic builds upon, acts upon, associates with, and/or completes the visible graphic once the hidden graphic is made visible in the post-application state. Without wishing to be limited to the specific embodiments listed, examples of interactively interrelated graphics can include: a visible seascape and hidden jumping fish; a visible umbrella and hidden rain clouds; visible musical notes and hidden musician; a visible telescope and hidden stars, planets, and the like; a visible alien and a hidden UFO; a visible racecar and hidden race flag(s); a visible flower and a hidden rainbow; a visible portion of a character (i.e., the fireman's trousers and boots) and a hidden portion of the character (i.e., the fireman's coat and helmet); and a visible swimming pool and a hidden character diving into the pool.

The visible graphic may be positioned within the front region, the crotch region, and/or the back region. In one particular embodiment, the visible graphic on the front region may illustrate the front view of a scene and the visible graphic on the back region may illustrate the rear view of the same scene as pictured on the front region. For example, the visible graphic on the front region may be the face of a teddy bear and the visible graphic on the rear region is the back of the teddy bear's head. Likewise, hidden graphics may also appear in the front region and the back region of the pull-on garment, and the hidden graphics may also depict the front and back of the same scene. Hidden graphics may be positioned within the continuous belt zone such that when the pull-on garment is in its furled pre-application state the hidden graphics are not visible.

Figure 8A:
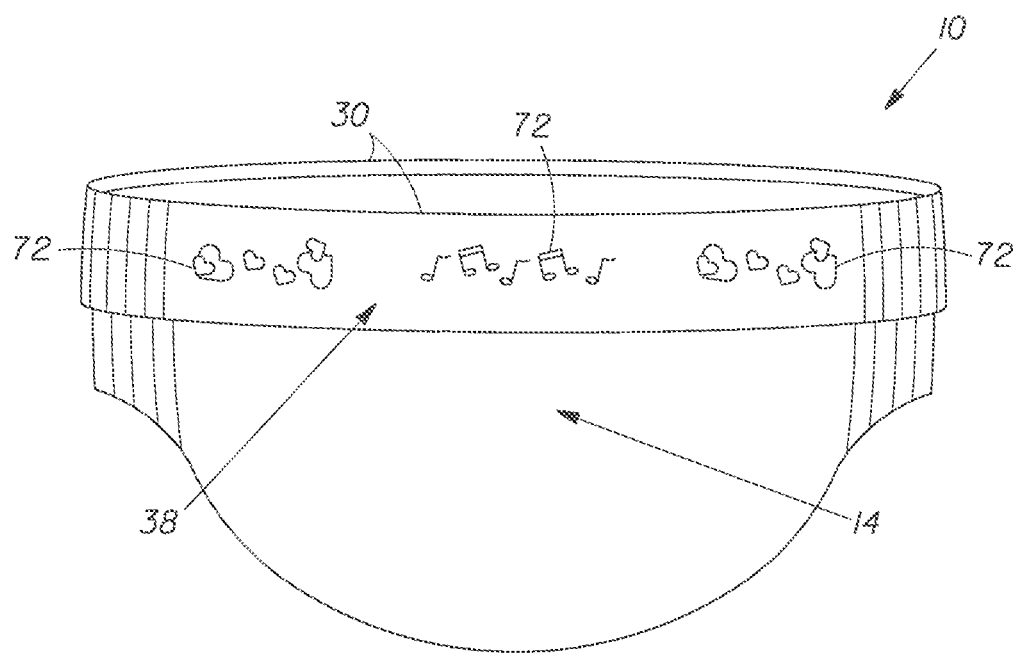
FIG. 8a is one embodiment of a disposable pull-on garment of the present invention in a pre-application state and having visible graphics.
Figure 8B:
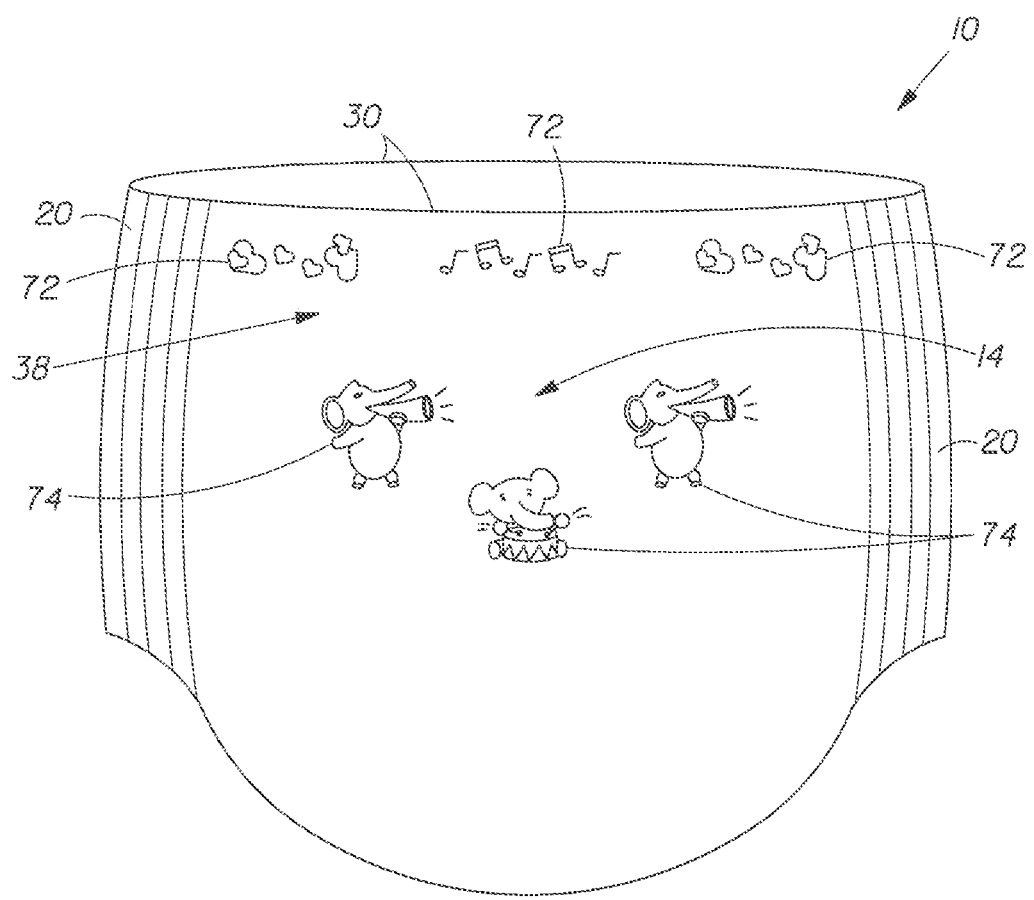
FIG. 8b is one embodiment of a disposable pull-on garment of the present invention in a post-application state and having visible and hidden graphics.

FIGS. 8*a* and 8*b* illustrate one embodiment of the garment 10 of the present invention with hidden graphics 74 and visible graphics 72. FIG. 8*a* shows a garment 10 in a pre-application state with the continuous belt 38 being furled with two longitudinal pleats in a manner substantially similar to that presented in FIGS. 5*a* and 5*b* (i.e., for this embodiment, the waist edge 30 remains the uppermost edge of the garment 10 in both the pre-application and post application states). The side panels 20 are foreshortened by the pleating. In the pre-application state, the garment 10 may have one or more visible graphics 72, which may be in the front region 14 of the garment 10. The garment 10 may contain one or more hidden graphics 74 that are concealed from view by the pleating of the continuous belt 38. FIG. 8*b* shows the garment 10 of FIG. 8*a* in the post-application state with the side panels 20 fully unfurled and extended. Upon application of the garment 10 and unfurling of the continuous belt 38, both the visible graphics 72 and hidden graphics 74 are visible.

Another embodiment of the present invention is directed toward a method of applying the pull-on garment of the present invention. In particular, the method is directed toward self-application of the pull-on by an infant. It is envisioned that self-application may be a component of a larger toilet training regimen. The term "toilet training regimen" refers generally to the process whereby a caregiver transitions a diaper wearing infant to become self-sufficient in disposing of bodily waste by use of the toilet. The pull-on garment provides a milestone for an infant who is developing an independence from the caregiver since self-application of an undergarment marks self-sufficiency. The pull-on garments of the present invention facilitate self-application by reducing the length of the side panel. The reduced length is believed to result in reduced shear force experienced by the infant during application. Furthermore, the continuous belt with its reduced pre-application side panel length, especially in rolled and folded embodiments, offers a convenient grip point to which the infant may clutch.

The pull-on garment is provided to the infant in the pre-application state such that the pull-on garment has a pre-application side panel length $L_i$. The infant dons the pull-on garment by inserting his or her legs into the waist opening and through the leg openings. The pull-on is raised up the infant's legs to a point where the crotch region of the pull-on is proximate or in contact with the infant's crotch. Once the pull-on diaper is raised and sung against the infant's crotch, the furled continuous belt is unfurled. Given the particular embodiment, unfurling may involve unrolling, unfolding, or extending the particular method of furling used. By unfurling the continuous belt, the side panel is lengthened such that waist edge ideally encircles the infant's waist and hips. In this post-application state, the pull-on garment is ideally properly positioned and snug to the infant's body.

Furthermore, as mentioned above, self-application of the pull-on garment of the present invention may be one component of a more holistic toilet training regimen. An exemplary toilet training regimen involves a three phase transition from diapers to pull-on garments of the present invention to a traditional nonabsorbent undergarment. The phases need not necessarily be sequential and may, given the unique needs of any given infant, be intermittent or omitted. Furthermore, the phase may not be discrete; one or more phase may overlap another phase.

In one phase, the infant is gradually introduced to the pull-on garment by initial application and increased wear time of the training pant. The wear time of the pull-on garment is increased throughout the phase such that an infant begins the phase wearing a diaper almost exclusively and continuously and ends the phase wearing the pull-on garment almost exclusively and continuously. During this phase, proper application of the pull-on garment may be taught by a caregiver. Preferably, the teaching will highlight appropriate application and unfurling of the pull-on garment of the present invention. In particular, the infant may be instructed on how to don the article and unfurl the furled continuous belt.

In another phase, the infant is gradually introduced to a traditional less absorbent undergarment by initial application and increased wear time of the undergarment. The wear time of the undergarment is increased throughout the phase such that an infant begins the phase wearing a pull-on garment almost exclusively and continuously and ends the phase wearing the undergarment almost exclusively and continuously.

In yet another phase, the infant is taught by the caregiver to use the toilet instead of soiling the article (e.g., the diaper, pull-on garment, or the undergarment) worn by the infant. A caregiver utilizes a variety of behavioral modifications to achieve the goal of toilet use by the infant for urination and bowel movements. Behavioral modifications may involve using a "potty seat" (e.g., a child-sized self-contained portable toilet, a child-sized seat applied to a toilet, etc.), periodically setting the infant on the toilet, demonstrating the use of the toilet, reminding the infant to use the toilet, rewarding the infant for using the toilet including verbal praise and affection, talking to the infant about toilet use, re-education and correction if the infant soils him or herself, setting goals for the infant, providing other instructional material to the child such as books or audio/visuals, and combinations thereof. This phase is ideally partially concurrent with at least one of the proceeding two phases. Completion of this phase is achieved by the infant being relatively autonomous in the predominately exclusive use of the toilet for urination and bowel movements. Being relatively autonomous means that the infant recognizes when toilet use is necessary, can disrobe such that the toilet may be used, and can use the toilet. Predominately exclusive use of the toilet recognizes that, as with any training, an infant may forget, have accidents, or lapse into pre-toilet training behavior. Completion of this toilet-use phase need not coincide with any of the previously mentioned phases.

In another embodiment, a plurality of pull-on garments of the present invention may be packaged in a kit. The kit may comprise a plurality of pull-on garment having a pre-foreshortened side panel. The kit enables a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous pull-on garments bound together as an entity and covered by a thermoplastic film overwrap as disclosed in U.S. Pat. No. 5,934,470 issued to Bauer et al. on Aug. 10, 1999. The thermoplastic film cover ideally contains an opening means to allow removal of a portion of the thermoplastic film cover and access to the pull-on garments. A typical opening means includes a substantially continuous line of weakness, preferably perforations within the thermoplastic film cover. An exemplary opening means is presented in U.S. Pat. No. 5,036,978 issued to Frank et al. on Aug. 6, 1991.

While a preferred kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of pull-on garments. Other particularly preferred packages and methods for packaging are disclosed in U.S. Pat. No. 5,050,742 issued to D. R. Muckenfuhs on Sep. 24, 1991; and U.S. Pat. No. 5,054,619 issued to D. R. Muckenfuhs on Oct. 8, 1991. Furthermore, a kit may contain multiple overwraps. For example, a plurality of pull-on garments of the present inventions may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Furthermore, in another preferred embodiment, the kit may contain an instruction to a caregiver. The instruction may include directions, guidance, counseling, strategies, and verbal or non-verbal teachings (including graphical representations) provided to the caregiver regarding a toilet training regimen for the infant. Preferably, the instruction discloses a suggested method (e.g., the method as disclosed above) that a caregiver may use in transitioning the infant away from diaper use and toward toilet use. At least part of the instruction describes the use of the pull-on garment of the present application as a transitioning tool in training.

EXAMPLE

A pull-on garment may be formed as disclosed in U.S. Pat. No. 5,569,234 to Buell et al. The garment may have an overall length of approximately 46 cm and a width within the crotch region of approximately 14.5 cm. The core is preferably hourglass-shaped with an overall length of 34 cm and a width within the crotch region of approximately 8.0 cm. The core is positioned equidistant from the edges of the garment such that the edge of the core is approximately 6.0 cm from the waist edge in both the front and back regions.

The garment exhibits a folded continuous belt comprising three folds directed radially outward (i.e., folding done toward the garment-facing surface of the pull-on garment). The entire circumference of the continuous belt is folded radially outward. The resulting first fold may be approximately 2.0 cm in length. The entire circumference of the continuous belt may be folded radially outward a second time such that the first fold is enclosed by the second fold. The resulting second fold may be approximately 2.25 cm in length. The entire circumference of the continuous belt zone may be folded radially outward a third time such that the second fold is enclosed by the third fold. The resulting third fold may be approximately 2.5 cm in length. The resulting three fold design resembles that illustrated by FIG. 4b. The pre-application side panel length of the pull-on garment with three folds is approximately 3.25 cm. Once the garment is applied and unfurled, the post-application side panel length is approximately 10 cm.

All documents cited in the Detailed Description are in relevant part incorporated herein by reference; the citation of any document is not to be construed as an admission that it is prior art with respect to the present invention.

While particular embodiments of the present invention have been illustrated and described, it would be obvious to those skilled in the art that various other changes and modification can be made without departing from the spirit and scope of the invention. It is therefore intended to cover in the appended claims all such changed and modification that within the scope of this invention. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

What is claimed is:

1. A pull-on wearable article comprising:
    a front region;
    a back region opposite the front region;
    a crotch region disposed between the front region and the back region, wherein the crotch region comprises two opposing longitudinal edges;
    a chassis comprising an absorbent core extending from the front region to the back region, the absorbent core comprising a front end edge and a back end edge;
    wherein the front region extends laterally outward beyond side edges of the chassis and the back region extends laterally outward beyond side edges of the chassis;
    wherein the front region comprises a first front edge and a second front edge and the back region comprises a first back edge and a second back edge;
    wherein a portion of the front region and a portion of the back region abut to form a first seam and a second seam such that the front region and the back region are configured to form a continuous belt, a first leg opening, and a second leg opening;
    wherein at least one of the front region and the back region comprise an elastic member;
    a folded continuous belt portion comprising a fold and including at least a first outer nonwoven layer of the front region and at least a second outer nonwoven layer of the back region, wherein the folded continuous belt portion extends about a circumference of the continuous belt when positioned on the wearer, and wherein the folded continuous belt portion comprises an upper edge in the front and back regions such that a distal end of each of the first outer nonwoven layer and the second outer nonwoven layer is disposed between the upper edge and the front and back end edges of the absorbent core, respectively; and
    wherein the folded continuous belt comprises a first portion extending laterally between the first seam and the second seam and extending longitudinally between the upper edge and the distal end of the first outer nonwoven layer, the first portion has a first longitudinal distance measured from the upper edge to the distal end of the first outer nonwoven layer;
    wherein the folded continuous belt comprises a second portion extending laterally between the first seam and the second seam and extending longitudinally between the upper edge and the distal end of the second outer nonwoven layer, the second portion has a second longitudinal distance;
    wherein each of the first front edge, the second front edge, the first back edge, and the second back edge extend in a longitudinal direction perpendicular to at least one of the distal end of the first outer nonwoven layer and the distal end of the second outer nonwoven layer;

wherein the first longitudinal distance is substantially uniform relative to the second longitudinal distance;

wherein the first seam comprises discrete spaced bonds extending in the longitudinal direction from the first leg opening to the upper edge;

wherein the second seam comprises discrete spaced bonds extending in the longitudinal direction from the second leg opening to the upper edge.

2. The pull-on wearable article of claim 1, wherein the distal end of each of the first outer nonwoven layer and the second outer nonwoven layer is disposed on at least one of a garment facing surface and a wearer facing surface.

3. The pull-on wearable article of claim 1, wherein the first longitudinal distance is about 2.0 cm.

4. The pull-on wearable article of claim 1, further comprising a graphic disposed on a wearer facing surface of the wearable absorbent article.

5. The pull-on wearable article of claim 1, wherein the elastic member comprises one or more strands.

\* \* \* \* \*